United States Patent
Korporaal et al.

(10) Patent No.: US 11,857,356 B2
(45) Date of Patent: Jan. 2, 2024

(54) METHOD AND DEVICE FOR RECORDING MEDICAL IMAGES

(71) Applicant: Siemens Healthcare GmbH, Erlangen (DE)

(72) Inventors: Johannes Georg Korporaal, Forchheim (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 521 days.

(21) Appl. No.: 15/115,921

(22) PCT Filed: Feb. 6, 2015

(86) PCT No.: PCT/EP2015/052484
§ 371 (c)(1),
(2) Date: Aug. 2, 2016

(87) PCT Pub. No.: WO2015/124441
PCT Pub. Date: Aug. 27, 2015

(65) Prior Publication Data
US 2017/0181719 A1   Jun. 29, 2017

(30) Foreign Application Priority Data
Feb. 21, 2014 (EP) .................................. 14156162

(51) Int. Cl.
*A61B 6/00* (2006.01)
*A61B 6/03* (2006.01)
(Continued)

(52) U.S. Cl.
CPC .............. *A61B 6/504* (2013.01); *A61B 5/055* (2013.01); *A61B 6/032* (2013.01); *A61B 6/44* (2013.01);
(Continued)

(58) Field of Classification Search
CPC ......... A61B 6/504; A61B 5/055; A61B 6/032; A61B 6/44; A61B 6/4441; A61B 6/481;
(Continued)

(56) References Cited

U.S. PATENT DOCUMENTS 6,240,311 B1 * 5/2001 Prince .................... A61B 5/411
324/307
6,876,720 B2 * 4/2005 Tsuyuki ................. A61B 6/032
378/4

(Continued)

FOREIGN PATENT DOCUMENTS

CN       1471980 A      2/2004
CN     101185591 A      5/2008
(Continued)

OTHER PUBLICATIONS

Subject Matter Eligibility Example 40 (Year: 2019).*
(Continued)

*Primary Examiner* — Joseph M Santos Rodriguez
*Assistant Examiner* — Amy Shafqat
(74) *Attorney, Agent, or Firm* — Harness, Dickey & Pierce, P.L.C.

(57) ABSTRACT

A method is disclosed for recording medical images of the human body or that of an animal. The method includes scanning for acquiring data and signaling the start and/or end of a manual administration of a contrast medium in temporal relation to the scan for acquiring data.

38 Claims, 2 Drawing Sheets

(51) Int. Cl.
*A61B 8/08* (2006.01)
*A61B 5/055* (2006.01)
*A61M 5/00* (2006.01)
*G01R 33/56* (2006.01)
*G01R 33/28* (2006.01)

(52) U.S. Cl.
CPC ............ *A61B 6/4441* (2013.01); *A61B 6/481* (2013.01); *A61B 8/481* (2013.01); *A61B 8/483* (2013.01); *A61M 5/007* (2013.01); *G01R 33/283* (2013.01); *G01R 33/5601* (2013.01)

(58) Field of Classification Search
CPC ........... A61B 8/483; A61B 8/481; A61B 8/08; A61B 6/03; A61B 6/00; A61M 5/007; A61M 5/00; A61M 5/168; A61M 2205/581; A61M 2205/583; A61M 5/14546; G01R 33/283; G01R 33/5601; G01R 33/28; G16H 20/17; G16H 20/10; G16H 20/00; G06F 19/3468
See application file for complete search history.

(56) References Cited

U.S. PATENT DOCUMENTS

| | | | |
|---|---|---|---|
| 7,853,309 B2 | 12/2010 | Ichihara et al. | |
| 7,974,682 B2* | 7/2011 | Gonzalez Molezzi | ..................... A61B 5/7285 600/432 |
| 8,676,297 B2* | 3/2014 | Benndorf | ............... A61B 6/504 600/425 |
| 9,597,051 B2* | 3/2017 | Gatayama | .............. A61B 6/545 |
| 9,848,843 B2* | 12/2017 | Grass | .................... A61B 6/486 |
| 10,010,305 B2* | 7/2018 | Tsuyuki | ................. A61B 6/032 |
| 2004/0024361 A1* | 2/2004 | Fago | ................. A61M 5/31525 604/113 |
| 2004/0068176 A1 | 4/2004 | Kuth | |
| 2007/0100282 A1* | 5/2007 | Small | ................ A61M 5/14566 604/151 |
| 2008/0119715 A1 | 5/2008 | Gonzalez Molezzi et al. | |
| 2009/0253984 A1 | 10/2009 | Yui et al. | |
| 2010/0292570 A1* | 11/2010 | Tsukagoshi | ............ A61B 6/032 600/431 |
| 2011/0130668 A1 | 6/2011 | Ohyu et al. | |
| 2013/0010922 A1 | 1/2013 | Taguchi et al. | |
| 2013/0012814 A1 | 1/2013 | Taguchi et al. | |
| 2014/0093043 A1* | 4/2014 | Nakatsugawa | ........ A61B 6/481 378/62 |
| 2014/0163368 A1* | 6/2014 | Rousso | ................. G01T 1/1615 600/436 |
| 2016/0089100 A1 | 3/2016 | Korporaal | |

FOREIGN PATENT DOCUMENTS

| | | |
|---|---|---|
| CN | 101548887 A | 10/2009 |
| CN | 101889872 A | 11/2010 |
| CN | 102038515 A | 5/2011 |
| CN | 102665563 A | 9/2012 |
| CN | 102695454 A | 9/2012 |
| CN | 103315740 A | 9/2013 |
| CN | 105283131 A | 1/2016 |
| DE | 10302636 A1 | 12/2003 |
| DE | 102011004641 A1 | 8/2012 |

OTHER PUBLICATIONS

Chinese Office Action and English translation thereof dated Jul. 3, 2018.
International Search Report and Written Opinion dated Jun. 3, 2015.
Office Action issued in Chinese Application No. 201580009365.3 dated Mar. 8, 2019 and English translation thereof.
Office Action dated Nov. 22, 2019 in Chinese Application No. 201580009365.3.
Office Action for Chinese Application No. 201580009365.3 dated Jun. 22, 2020 and English translation thereof.

* cited by examiner

METHOD AND DEVICE FOR RECORDING MEDICAL IMAGES

PRIORITY STATEMENT

This application is the national phase under 35 U.S.C. §371 of PCT International Application No. PCT/EP2015/052484 which has an International filing date of Feb. 6, 2015, which designated the United States of America and which claims priority to European patent application number EP 14156162.1 filed Feb. 21, 2014, the entire contents of which are hereby incorporated herein by reference.

FIELD

An embodiment of invention generally relates to a method and/or to an apparatus for capturing medical images, in particular via computed tomography (CT) or magnetic resonance imaging (MRI). In particular, an embodiment of the invention relates to capturing two-dimensional or three-dimensional images of the inside of a human body or of the body of an animal, which images are meant to show or display blood vessels in particular.

BACKGROUND

It is known to inject a contrast agent in order to improve the display of blood vessels. Medical imaging using a contrast agent has the fundamental problem here of achieving contrast enhancement in vessels or tissue that is consistent over time or simultaneous with data acquisition while aiming in particular to use a minimum possible amount of contrast agent to achieve contrast enhancement. Contrast agents, like the radiation dose, have a potentially harmful effect on the patient, which is why it makes sense to keep levels to a minimum. Cost is also a factor when using a contrast agent, and therefore reducing the amount of contrast agent is also advantageous financially to organizations that operate imaging systems.

The contrast agent is usually injected on the basis of a protocol, which is specified according to indication, organ under examination and possibly according to patient parameters such as age, weight, BMI, etc. This protocol is characterized e.g. by amount of contrast agent, injection rate and start of the injection relative to the scan. The injection itself is then implemented by an injection device, the parameters of which are set by the protocol.

The start point of the scan can also be determined on the basis of what is known as a bolus trigger. In this case, images are captured in a time sequence at a predefined position, and the scan is triggered when a predefined attenuation value (CT value, gray level) is exceeded in a defined region of the image, also known as the region of interest (ROI), e.g. in a large vessel. This means that the scan procedure can take into account the patient-dependent time between start of the injection and arrival of the contrast agent in the region of interest in the body.

Sometimes, however, the injection is actually performed manually (injection using a syringe), in which case it is very likely that start of the injection, duration and amount of contrast agent will be far removed from the optimum timing and minimum amount of contrast agent. For example, there is no need to continue to inject in a time period before the scan end equal to the time between injection start and arrival of the bolus in the region of interest, because the contrast agent injected in this time period will no longer have an effect on the image (owing to its delayed arrival in the region of interest). Without further information, it is practically impossible to make an estimate from an indicator (e.g. lamp or acoustic signal) signaling the operation of the acquisition apparatus (scan in progress, e.g. using X-rays). This results in inefficient use of contrast agent and increases the risk for the patient and the costs of the examination.

SUMMARY

At least one embodiment of the invention defines an apparatus and/or a method for diagnostic imaging that reduces or even minimizes the risk for the patient and improves the economic efficiency. In particular, at least one embodiment of the invention improves or even optimizes the contrast administration where there is no assistance from special injectors or injection devices (manual contrast administration).

At least one embodiment is directed to a method and at least one embodiment is directed to an apparatus. The subject matter of the claims and of the following description, in particular in conjunction with the figures, contains example embodiments of the invention.

The method according to an embodiment of the invention for capturing medical images of the human body or body of an animal comprises:
(1) performing a data-acquisition scan, and
(2) signaling the start and/or the end of a manual contrast administration relative in time to the data-acquisition scan.

An embodiment of the invention also relates to a method for determining a point in time for outputting a signal that signals a start and/or an end of the administration of a contrast agent, and for determining a point in time for the start or the end of an operating state of a medical machine at a predefined point in time related in time to the signal.

An embodiment of the invention also relates to a method for operating a medical machine, wherein
a signaling unit signals a start and/or an end of the administration of a contrast agent,
an operating state of the medical machine is timed to start and/or end with respect to a signal that is output by the signaling unit.

An apparatus according to an embodiment of the invention is for capturing medical images of the human body or body of an animal comprises an acquisition unit, which is designed to perform a data-acquisition scan, and a signaling unit, which is coupled to the acquisition unit and is designed to output, relative in time to the data-acquisition scan, a signal for starting and/or stopping a manual contrast administration.

An apparatus according to an embodiment of the invention is for controlling the acquisition of medical images, which apparatus comprises a unit that is designed to control, in particular to start and/or to end, a data-acquisition scan, and a signaling unit, which is coupled to said unit and is designed to output, relative in time to the data-acquisition scan, a signal for starting and/or stopping a manual contrast administration.

An apparatus according to an embodiment of the invention is for a medical machine (apparatus for capturing medical images), in particular of a computed tomography machine, comprising
a signaling unit, which is designed to output a signal that signals a start and/or an end of the administration of a contrast agent, and a unit that is designed to control the start and/or the end of an operating state of the medical machine at a predefined time related in time to a signal that is output by the signaling unit.

BRIEF DESCRIPTION OF THE DRAWINGS

The invention is described further below with reference to an example embodiment, which is depicted in the accompanying figures, in which.

DETAILED DESCRIPTION OF THE EXAMPLE EMBODIMENTS

Figure 1:
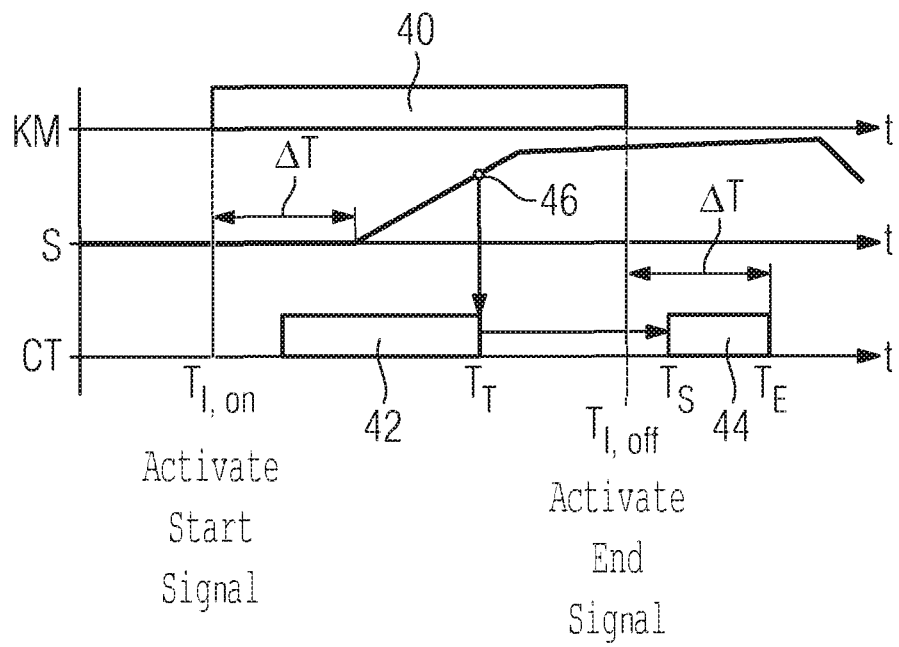
FIG. 1 is a diagram for illustrating the method according to an example embodiment of the invention.

The method according to an embodiment of the invention for capturing medical images of the human body or body of an animal comprises:
(3) performing a data-acquisition scan, and
(4) signaling the start and/or the end of a manual contrast administration relative in time to the data-acquisition scan.

The apparatus according to an embodiment of the invention for capturing medical images of the human body or body of an animal comprises an acquisition unit, which is designed to perform a data-acquisition scan, and a signaling unit, which is coupled to the acquisition unit and is designed to output, relative in time to the data-acquisition scan, a signal for starting and/or stopping a manual contrast administration.

An apparatus according to an embodiment of the invention is for controlling the acquisition of medical images, which apparatus comprises a unit that is designed to control, in particular to start and/or to end, a data-acquisition scan, and a signaling unit, which is coupled to said unit and is designed to output, relative in time to the data-acquisition scan, a signal for starting and/or stopping a manual contrast administration.

An idea of at least one embodiment of the invention is to signal the start and/or the end of a manual contrast administration (contrast agent is administered without controlled and/or automatic injector, e.g. it is administered by a standard commercial syringe) relative in time to a scan, which in particular is to be performed subsequently. The signaling unit may be in particular a visual, haptic and/or acoustic signaling unit, which is connected to the acquisition unit (for example CT machine) and gives instructions on the manual (non-automated) administration of contrast agent, e.g. using a syringe. The instruction may thus be a light signal and/or acoustic signal, for example. This may instruct, for instance, continuous pressing of the syringe plunger and/or stopping the injection. In particular, different signals can be provided for this purpose. It is also possible that the start of a signal signals the start of the contrast administration, and the end of the signal signals the end of the contrast administration. Thus the contrast agent is then meant to be administered in particular precisely during the output of the e.g. visual or acoustic signal.

The apparatus according to at least one embodiment of the invention and the method according to at least one embodiment of the invention provide considerable assistance during manual injection of contrast agent. This has a positive effect on the expected image quality, because it is possible to make better use of the contrast-enhancing effect. At the same time, it increases the safety of the patients because the amount of contrast agent is kept lower than for an injection without assistance. In environments that lack the financial means for purchasing/operating a controlled injector, for example, there is no need to compromise on patient safety.

In an example embodiment of the method, the signaling of the start of the manual contrast administration is timed with respect to a manual or automatic start of the acquisition process.

The signal, which instructs a start of the manual administration of contrast agent, can be triggered, for example, after a predetermined or preset time delay after switch-on of the acquisition apparatus or an activation and/or a start of the acquisition procedure. In principle, any point in time can be selected for signaling the start of the contrast administration. What is important is that this point in time is known so that it is possible to calculate further values therefrom, for instance the time until a bolus arrives at a region of interest, the start of the data scan or the duration of the contrast administration.

In another example embodiment of the invention, triggering the data-acquisition scan is timed with respect to the signaled start of the manual contrast administration.

A best possible start time for the data-acquisition scan can be chosen using the known time for the start of the contrast administration (assuming that this starts at the time of the start signal). For instance, a delay to the scan start with respect to the injection start can be set, if applicable according to further parameters such as, for example, patient size, patient weight and/or spatial relationship between injection location and ROI. Thus the data acquisition starts at a predetermined time delay after the signal for starting the contrast administration. It is also possible that triggering the scan comprises a bolus triggering, i.e. initiating the process of bolus triggering (or start of a monitoring scan) is timed with respect to the signaled start of the manual contrast administration. For example, the monitoring scan can be performed simultaneous to, or at a predetermined delay with respect to, signaling the start of the contrast administration.

In another example embodiment, the point in time of signaling the end of the manual contrast administration is calculated.

For example, a defined injection duration can be provided. The end of the contrast-agent injection is then calculated on the basis of the signaled start time for the contrast-agent injection and the defined injection duration.

In another example embodiment, the signalling of the end of the manual contrast administration is timed with respect to a characteristic time interval $\Delta T$, wherein the characteristic time interval $\Delta T$ is a time difference between the arrival of contrast agent at a predefined position in the body (ROI) and the point in time of signaling the start of the manual contrast administration.

The characteristic time $\Delta T$ is hence the time that elapses for a patient between start of the injection (assuming that the injection is started at the time of the signaling) and arrival of the contrast agent at the desired position in the body. The signaling of the end of the contrast administration preferably takes place at the latest at a time that lies in advance of the end of the scan by the magnitude of the time interval $\Delta T$.

In an example embodiment, the time interval $\Delta T$ is estimated. An empirical value determined from analyzing a patient collective is preferably used for the estimate. This analysis preferably additionally takes into account additional patient parameters such as size and weight, for instance.

In an alternative embodiment, the time interval ΔT is calculated. In particular, it is preferred that the time interval ΔT is determined on the basis of a bolus triggering. In this case, the time interval ΔT in particular equals the difference between a time at which a defined threshold value (attenuation value, gray level, enhancement) is attained and the point in time of signaling the start of the contrast administration.

Thus the time interval ΔT is preferably calculated on the basis of a monitoring scan at the predefined position in the body. The arrival of a bolus in the region of interest (ROI) is detected by the monitoring scan, and therefore the time delay with respect to the start of the contrast-agent injection can be determined.

In another example embodiment of the method according to the invention, the calculation of the time interval ΔT takes into account the point in time of signaling the start of the manual contrast administration.

More preferably, the time interval ΔT is calculated as the difference between attaining a defined threshold value (trigger) and the point in time of signaling the start of the manual contrast administration.

Alternatively or additionally, the point in time of signaling the end of the manual contrast administration can be calculated on the basis of a flow model.

The point in time of signaling the end of the manual contrast administration, or the time interval ΔT, can be determined or calculated in particular using a hydrodynamic or pharmacokinetic flow model. This could then also take into account, for instance, the length of time for the already injected amount of contrast agent. In addition, the point in time of signaling the start of the contrast administration and/or the trigger signal (attaining a defined threshold value) is preferably also used.

In another example embodiment of the invention, an advance signal is produced before signaling the start and/or end of the manual contrast administration. The advance signal is used in particular for eliminating, or more precisely taking into account, response times. For instance, the advance signal can be triggered a predefined time before the actual signal.

In an example embodiment, the advance signal comprises a countdown. For example, a countdown can be performed before the actual signaling (before the signal for starting and/or stopping the contrast administration), for instance a countdown using color coding (light) or frequency coding of an audio tone (acoustic signal), in order to hit the start point and/or end point of the manual injection more closely.

In terms of the apparatus, in an example embodiment of the invention, the apparatus comprises a processing unit, which is designed to calculate a start time and/or an end time for the manual contrast administration.

In an example embodiment of the invention, the processing unit is designed to calculate the end time for the manual contrast administration on the basis of a characteristic time interval ΔT, wherein the characteristic time interval ΔT is a time difference between the arrival of contrast agent (a contrast-agent bolus) at a predefined position in the body and the point in time of signaling the start of the manual contrast administration.

FIG. 1 shows an example of the sequence of a diagnostic imaging process using contrast administration. The bottom region shows the timing diagram of a CT scan (CT). What is known as a monitoring scan 42 is performed first, which is used to trigger the actual examination scan 44. In this scan, images are captured in a time sequence. The scan 44 is triggered when a predefined threshold value 46 (signal level, gray level, attenuation value or CT value) is exceeded in a defined region of interest (ROI, e.g. a large vessel). The scan 44 in this case starts at a predefined delay after the predefined threshold value 46 is attained. The scan 44 is started at the time $T_S$ and ends at the time $T_E$.

The central region of the diagram shows the signal level S (gray level, attenuation value or CT value) in the timing diagram. The administration of contrast agent (KM) causes the signal level S to rise and to attain a predefined threshold value at the point 46. The monitoring scan 42 ends and the examination scan 44 is triggered when the threshold value 46 is attained. The examination scan 44 then starts with a delay after being triggered.

The top region of the diagram shows schematically the contrast agent KM, or more precisely the injection of the contrast agent. The injection of a contrast-agent bolus 40 starts at the time $T_{I,on}$. The contrast agent is preferably injected at a constant rate in this process. The injection ends at the time $T_{I,off}$.

The method according to an example embodiment of the invention and the apparatus according to an example embodiment of the invention are used to signal to a user the time $T_{I,on}$ and/or the time $T_{I,off}$. Hence the user knows when he is meant to start and/or end the injection of a contrast-agent bolus.

The method according to an example embodiment of the invention in particular contains the following steps:

1. (Manually) activating the signal for instructing the start of the manual injection. The start of the injection $T_{I,on}$ is signaled at a certain delay after the, possibly manual, activation. In principle, any point in time can be selected for the time $T_{I,on}$, which preferably lies at a certain time interval after the switch-on and/or activation of the signal and/or of the apparatus. Signaling the start time of the injection is used in particular for activating the monitoring scan 42 and/or the scan 44 on the basis of this time.

2. Starting a bolus triggering or a monitoring scan, i.e. periodic sequence of scans at a predefined, sensible position in the body, and measurement of the signal levels (CT values) inside an ROI. Initiation of the start time of the bolus triggering is timed with respect to the time $T_{I,on}$ (for example simultaneously or at a predetermined delay).

3. On a defined threshold value 46 being attained (trigger):
   a) triggering the scan 44, preferably at a predefined delay, and
   b) calculating a characteristic time ΔT, which elapses for this patient between start of the injection and arrival of the contrast agent at the desired position in the body. The time interval between injection start ($T_{I,on}$) and attainment of the threshold value 46 ($T_T$) can be set as a conservative estimate for ΔT.

4. Calculating a time at which the injection can be stopped ($T_{I,off}$), e.g. as $T_{I,off}=T_E-\Delta T$, where $T_E$ denotes the end of the scan (=end of the radiation). Alternatively, the defined stop of the injection could also be calculated as $T_{I,off}=T_S-\Delta T$, where $T_S$ denotes the start of the scan (=start of the radiation).

5. Deactivating the signal at $T_{I,off}$, but at the latest at $T_E-\Delta T_{min}$, where $\Delta T_{min}$ is a sensible minimum time length for arrival of the contrast agent, which time length has been predefined e.g. from the analysis of a large patient collective.

6. Stopping the scan at $T_E$.

The switch-off time $T_{I,off}$ of the signal for the contrast-agent injection can advantageously also be calculated in step 4 using hydrodynamic or pharmacokinetic flow models.

These could then also take into account, for instance, the length of time for the already injected amount of contrast agent, and the trigger signal. This applies likewise to defining an optimum parameter ΔT (see step 3).

The method can also be used without bolus triggering, with the parameter ΔT being estimated in this case, for example. In the simplest case, it could be set to equal $ΔT_{max}$ or $ΔT_{min}$, which is the maximum or minimum expected arrival time length obtained from the analysis of a large patient collective. Again in this case, patient size and patient weight could be included in order to obtain a better estimate.

The signal for manual injection can be made, for example, visually (e.g. using a lamp) and/or acoustically (signal tone). An enhanced indication for eliminating response times is also possible. After calculating $T_{I,off}$, a countdown can be performed e.g. from the current instant in time, which countdown, for example, can be color-coded (light) or coded in terms of the frequency of the audio tone (acoustic signal). This makes it easier for the user to hit the start point and/or end point of the manual injection more closely.

As an alternative to an injection stop based on the parameter ΔT, a predefined injection duration (e.g. ten seconds) could also be set in order to assist the manual injection. This could be done, for example, by making the signal last as long as the desired injection duration.

Figure 2:
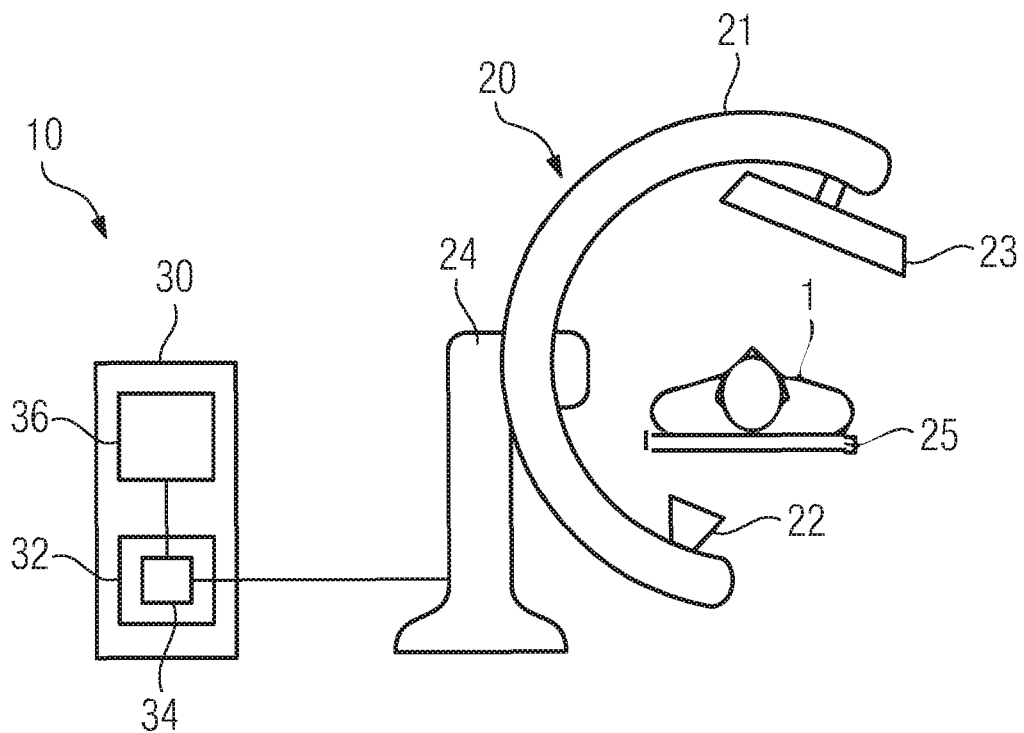
FIG. 2 shows an apparatus according to an example embodiment of the invention for capturing medical images.

FIG. 2 shows an example embodiment of an apparatus 10 according to the invention for implementing the method according to the invention. The apparatus 10 comprises an acquisition unit 20, which in this case is an X-ray machine, in particular a C-arm machine. The acquisition unit 20 comprises an X-ray source 22 and an X-ray detector 23, which are attached to the ends of a C-arm 21. The C-arm 21 can be tilted about a patient couch 25. The X-ray detector 23 is preferably a digital X-ray detector, which can produce digital X-ray images of a patient 1 lying on the patient couch 25. The C-arm 21 is mounted so that it can move on a stand 24.

The acquisition unit 20 is designed to capture two-dimensional projected images (fluoroscopy images) at short time intervals (preferably at least one image every two seconds). The acquisition unit 20 is controlled by a control unit 32. The control unit 32 is coupled to a signaling unit 36, which is designed to signal at least one signal for signaling the start of a manual injection of contrast agent and/or the end of such an injection. The signaling can be acoustic and/or visual, for example. The essential factor is that the injection is not controlled automatically.

A processing unit 34, which can be part of the control unit 32, is provided for calculating the time $T_{I,on}$ and/or the time $T_{I,off}$ (or for calculating the time interval ΔT). The processing unit 34 is designed to determine or to calculate the start time and/or the end time of the manual contrast administration. The signaling unit 36 is designed to output according to the start time and/or end time determined by the processing unit 34, a user-perceptible signal for starting and/or stopping the manual contrast administration.

Control unit 32 and signaling unit 36 can be part of a control apparatus 30, which can also be referred to as an apparatus 30 for instructing a manual contrast administration. The apparatus 30 forms a separate aspect of the invention. The apparatus 30 is designed to signal the start and/or the end of a manual contrast administration and to control in synchronization therewith the acquisition unit 20 (start and end of a monitoring scan 42 and/or of a (examination) scan 44).

An example embodiment of the invention can also be described in particular as follows:

A control apparatus for a medical machine (apparatus for capturing medical images), in particular of a computed tomography machine, comprising
  a signaling unit, which is designed to output a signal that signals a start and/or an end of the administration of a contrast agent, and
  a unit that is designed to control the start and/or the end of an operating state of the medical machine at a predefined time related in time to a signal that is output by the signaling unit.

A medical machine, in particular a computed tomography machine, comprising the control apparatus described above.

The signal in particular may be a haptically, acoustically and/or visually perceptible signal.

The point(s) in time for outputting the signal that signals the start and/or the end of the administration of a contrast agent can be determined as described above. Predetermined values for these point(s) in time can preferably be stored in the control apparatus.

The point(s) in time for the start or the end of the operating state of the medical machine can be determined as described above. Predetermined values for these point(s) in time can preferably be stored in the control apparatus.

Electronic storage, for instance, can be used for storing predetermined time points.

The operating state of the medical machine can be e.g. an operating state during which a monitoring scan or an examination scan is performed.

Different user-selectable points in time or combinations of points in time for outputting the signal that signals the start and/or the end of the administration of a contrast agent, and for the start or the end of the operating state of the medical machine, can be stored in the control apparatus for different examination protocols (e.g. depending on the region of interest (ROI), e.g. thorax, heart, predefined blood vessels), different contrast agents or different patient characteristics (e.g. male/female, weight, size, clinical condition, pulse, blood pressure, medication).

Alternatively, predetermined points in time can be adjusted according to different patient characteristics so that the points in time can be used to adapt defined intervals (e.g. the duration of an operating state) to a patient under examination.

An embodiment of the invention also relates to a method for determining a point in time for outputting a signal that signals a start and/or an end of the administration of a contrast agent, and for determining a point in time for the start or the end of an operating state of a medical machine at a predefined point in time related in time to the signal.

An embodiment of the invention also relates to a method for operating a medical machine, wherein
  a signaling unit signals a start and/or an end of the administration of a contrast agent,
  an operating state of the medical machine is timed to start and/or end with respect to a signal that is output by the signaling unit.

The times for the start and/or for the end of an interval can be indicated in particular by the start or end of a signal. In this respect, the term "signal" includes the start, the duration and the end of the signal, each taken independently.

Figure 3:
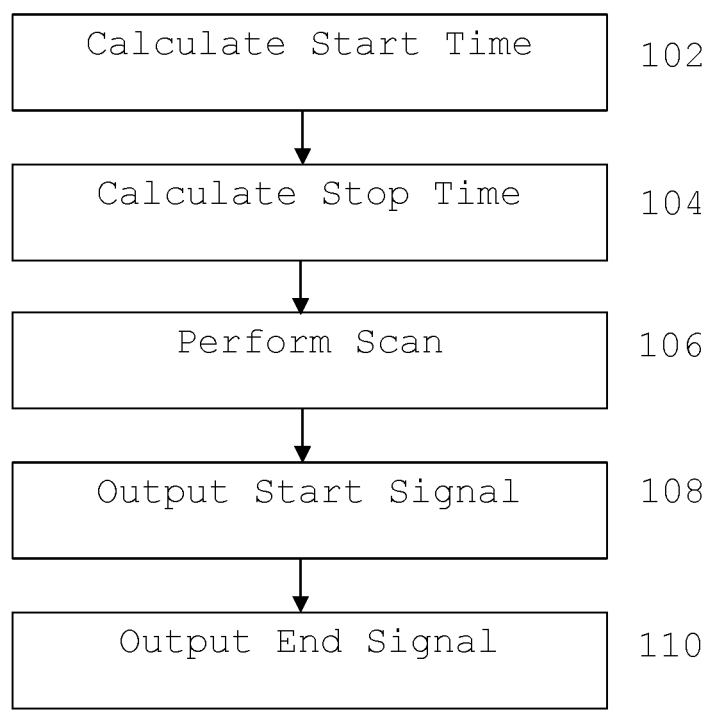
FIG. 3 shows a method performed by the apparatus of FIG. 2, according to an example embodiment.

Although the invention has been illustrated and described in greater detail using an example embodiment, the inven- FIG. 3 shows an example embodiment of a method performed by the apparatus 10. In operation 102, the method includes calculating a start time for manual contrast administration. In operation 104, the method includes calculating a time at which the injection can be stopped. In operation 106, the method includes performing an examination scan. In operation 108, the method includes outputting a signal for starting manual contrast administration. In operation 110, the method includes outputting a signal for ending manual contrast administration.

The invention claimed is:

1. A method for capturing medical images of a body, the body being a human body or a body of an animal, the method comprising:
   determining a start time for starting manual contrast administration;
   performing a monitoring scan including,
      detecting first medical imaging data corresponding to magnetic resonance data or x-ray data,
      producing first images of the body based on the magnetic resonance data or the x-ray data, and
      detecting a signal level at a defined position in the body from the first images;
   computing a first time interval based on a characteristic time interval between the start time for starting the manual contrast administration and a time at which the signal level at the defined position in the body reaches a threshold level;
   computing an end time for ending the manual contrast administration such that the end time for ending the manual contrast administration precedes an end of a medical imaging scan of the body by the first time interval;
   outputting a first advance signal at a first defined time before the start time for starting manual contrast administration;
   outputting a first indication at the start time instructing performance of the manual contrast administration;
   performing the medical imaging scan, a timing of at least one of the start time for starting the manual contrast administration, a beginning of the medical imaging scan or the end of the medical imaging scan being based on user-selected points in time, and the user-selected points in time being based on an examination protocol, a contrast agent or a patient characteristic;
   outputting a second advance signal after the computing, the second advance signal being a color-coded signal or an audio signal; and
   outputting a second indication at the end time for ending the manual contrast administration, the second indication instructing termination of the manual contrast administration, and the second advance signal being output at a second defined time before the second indication is output.

2. The method of claim 1, wherein each of the first indication and the second indication is a visual indication, a haptic indication or an acoustic indication.

3. The method of claim 1, wherein the computing the end time for ending the manual contrast administration computes the end time for ending the manual contrast administration according to $T_{I,off} = T_E - \Delta T$, $T_{I,off}$ representing the end time for ending the manual contrast administration, $T_E$ representing the end time for the medical imaging scan, and $\Delta T$ representing the first time interval, the first time interval being the characteristic time interval.

4. The method of claim 1, wherein the outputting the second advance signal outputs the second advance signal at a determined period before the outputting the second indication.

5. The method of claim 1, further comprising:
   terminating the manual contrast administration in response to the outputting the second advance signal and the outputting the second indication.

6. The method of claim 1, wherein the second advance signal is a user-perceptible signal indicating the end time for ending the manual contrast administration.

7. The method of claim 1, wherein the second advance signal is the audio signal, the audio signal being an audio countdown coded according to a frequency of an audio tone.

8. The method of claim 1, wherein the magnetic resonance data is first magnetic resonance data or the x-ray data is first x-ray data; and
   the performing the medical imaging scan comprises:
   detecting second medical imaging data corresponding to second magnetic resonance data or second x-ray data, wherein when the second medical imaging data is the second x-ray data, the second x-ray data corresponds to x-ray radiation that has passed through the body, and
   producing the medical images of the body based on the second medical imaging data.

9. The method of claim 1, wherein the outputting the first advance signal outputs the first advance signal at the first defined time for a predetermined period.

10. The method of claim 1, further comprising:
    outputting the second advance signal after outputting the first indication.

11. The method of claim 10, wherein the second advance signal is a countdown performed using the color-coded signal.

12. The method of claim 1, wherein the outputting the second advance signal outputs the second advance signal for a predetermined period.

13. The method of claim 12, wherein the predetermined period is a fixed period of time, a duration of the fixed period of time being based on a response time of a user.

14. The method of claim 1, wherein the determining determines the start time for starting the manual contrast administration based on a manual or automatic start of the medical imaging scan of the body.

15. The method of claim 14, further comprising:
    outputting the second advance signal after outputting the first indication.

16. The method of claim 15, wherein the second advance signal is a countdown performed using the color-coded signal.

17. The method of claim 1, wherein a start of the medical imaging scan of the body is based on the start time for starting the manual contrast administration.

18. The method of claim 17, further comprising:
    outputting the second advance signal after outputting the first indication.

19. The method of claim 18, wherein the second advance signal is a countdown performed using the color-coded signal.

20. An apparatus for capturing medical images of a body, the body being a human body or a body of an animal, the apparatus comprising:
  an acquisition unit configured to
    perform a monitoring scan including detecting first medical imaging data corresponding to magnetic resonance data or x-ray data, and
    perform a medical imaging scan of the body;
  a processing unit configured to
    determine a start time for starting manual contrast administration, a timing of at least one of the start time for starting the manual contrast administration, a beginning of the medical imaging scan or an end of the medical imaging scan being based on user-selected points in time, and the user-selected points in time being based on an examination protocol, a contrast agent or a patient characteristic,
    produce first images of the body based on the magnetic resonance data or the x-ray data,
    detect a signal level at a defined position in the body from the first images,
    compute a first time interval based on a characteristic time interval between the start time for starting the manual contrast administration and a time at which the signal level at the defined position in the body reaches a threshold level, and
    compute an end time for ending the manual contrast administration such that the end time for ending the manual contrast administration precedes the end of the medical imaging scan by the first time interval; and
  a signaling unit coupled to the acquisition unit, the signaling unit configured to
    outputting a first advance signal at a first defined time before the start time for starting manual contrast administration,
    output a first indication at the start time instructing performance of the manual contrast administration,
    output a second advance signal after computing the end time, the second advance signal being a color-coded signal or an audio signal, and
    output a second indication at the end time for ending the manual contrast administration, the second indication instructing termination of the manual contrast administration, and the second advance signal being output at a second defined time before the second indication is output.

21. The apparatus of claim 20, wherein the processing unit is configured to compute the end time for ending the manual contrast administration according to $T_{I,off}=T_E-\Delta T$, $T_{I,off}$ representing the end time for ending the manual contrast administration, $T_E$ representing the end time for the medical imaging scan, and $\Delta T$ representing the first time interval, the first time interval being the characteristic time interval.

22. The apparatus of claim 20, wherein
  the magnetic resonance data is first magnetic resonance data or the x-ray data is first x-ray data;
  and the acquisition unit is configured to perform the medical imaging scan including:
    detecting second medical imaging data corresponding to second magnetic resonance data or second x-ray data, wherein when the second medical imaging data is the second x-ray data, the second x-ray data correspond to x-ray radiation that has passed through the body, and
    producing the medical images of the body based on the second medical imaging data.

23. The apparatus of claim 20, wherein the signaling unit is configured to output the second advance signal for a predetermined period.

24. The apparatus of claim 23, wherein the predetermined period is a fixed period of time, a duration of the fixed period of time being based on a response time of a user.

25. The apparatus of claim 20, wherein the signaling unit is configured to output the second advance signal after outputting the first indication.

26. The apparatus of claim 25, wherein
  the second advance signal is a countdown performed using the color-coded signal.

27. A method, comprising:
  outputting a first advance signal at a first defined time before a start time for starting manual administration of a contrast agent to a body;
  outputting a first indication instructing performance of the manual administration of the contrast agent, the outputting the first indication outputs the first indication at the start time for starting the manual administration of the contrast agent;
  performing a monitoring scan including,
    detecting first medical imaging data corresponding to x-ray data,
    producing first images of a body based on the x-ray data, and
    detecting a signal level at a defined position in the body from the first images;
  computing a first time interval based on a characteristic time interval between the start time for starting the manual contrast administration and a time at which the signal level at the defined position in the body reaches a threshold level;
  outputting a second advance signal after computing an end time for ending the manual administration of the contrast agent, the second advance signal being a color-coded signal or an audio signal, the end time for ending the manual administration of the contrast agent preceding an end of an x-ray imaging scan of the body by the first time interval;
  outputting a second indication instructing termination of the manual administration of the contrast agent, the outputting the second indication outputs the second indication at the end time for ending the manual administration of the contrast agent, and the second advance signal being output at a second defined time before the second indication is output; and
  timing operation of an x-ray imaging device for performing the x-ray imaging scan based on the start time for starting the manual administration of the contrast agent, a timing of at least one of the start time for starting the manual administration of the contrast agent, a beginning of the x-ray imaging scan or the end of the x-ray imaging scan being based on user-selected points in time, and the user-selected points in time being based on an examination protocol, a contrast agent or a patient characteristic.

28. The method of claim 27, wherein the computing the end time for ending the manual administration of the contrast agent computes the end time for ending the manual administration of the contrast agent according to $T_{I,off}=T_E-\Delta T$, $T_{I,off}$ representing the end time for ending the manual administration of the contrast agent, $T_E$ representing the end time for the x-ray imaging scan, and $\Delta T$ representing the first time interval, the first time interval being the characteristic time interval.

29. The method of claim 27, wherein
the x-ray data is first x-ray data; and
the performing the x-ray imaging scan comprises:
- detecting second x-ray data, the second x-ray data corresponding to x-ray radiation that has passed through the body, and
- producing medical images of the body based on the second x-ray data.

30. The method of claim 27, further comprising:
terminating the manual administration of the contrast agent in response to the outputting the second advance signal and the outputting the second indication.

31. The method of claim 27, wherein the outputting the second advance signal outputs the second advance signal for a predetermined period.

32. The method of claim 31, wherein the predetermined period is a fixed period of time, a duration of the fixed period of time being based on a response time of a user.

33. An apparatus for capturing medical images of a body, the body being a human body or a body of an animal, the apparatus comprising:
- an x-ray imaging modality configured to,
  - perform a monitoring scan including detecting first medical imaging data corresponding to x-ray data, and
  - perform an x-ray imaging scan of the body; and
- a control device coupled to the x-ray imaging modality, the control device configured to
  - determine a start time for starting manual contrast administration,
  - produce first images of the body based on the x-ray data,
  - detect a signal level at a defined position in the body from the first images,
  - compute a first time interval based on a characteristic time interval between the start time for starting the manual contrast administration and a time at which the signal level at the defined position in the body reaches a threshold level,
  - compute an end time for ending the manual contrast administration such that the end time for ending the manual contrast administration precedes an end of the x-ray imaging scan by the first time interval, a timing of at least one of the start time for starting the manual contrast administration, a beginning of the x-ray imaging scan or the end of the x-ray imaging scan being based on user-selected points in time, and the user-selected points in time being based on an examination protocol, a contrast agent or a patient characteristic,
  - output a first advance signal at a first defined time before the start time for starting manual contrast administration,
  - output a first indication at the start time instructing performance of the manual contrast administration,
  - output a second advance signal after computing the end time, the second advance signal being a color-coded signal or an audio signal, and
  - output a second indication at the end time for ending the manual contrast administration, the second indication instructing termination of the manual contrast administration, and the second advance signal being output at a second defined time before the second indication is output.

34. The apparatus of claim 33, wherein the control device is configured to compute the end time for ending the manual contrast administration according to $T_{I,off} = T_E - \Delta T$, $T_{I,off}$ representing the end time for ending the manual contrast administration, $T_E$ representing the end time for the x-ray imaging scan, and $\Delta T$ representing the first time interval, the first time interval being the characteristic time interval.

35. The apparatus of claim 33, wherein the control device is configured to output the second advance signal for a predetermined period, the predetermined period being a fixed period of time, and a duration of the fixed period of time being based on a response time of a user.

36. The apparatus of claim 33, wherein
the x-ray data is first x-ray data; and
the x-ray imaging modality is configured to perform the x-ray imaging scan including:
- detecting second x-ray data, the second x-ray data corresponding to x-ray radiation that has passed through the body, and
- producing the medical images of the body based on the second x-ray data.

37. The apparatus of claim 33, wherein the control device is configured to output the second advance signal after outputting the first indication.

38. The apparatus of claim 37, wherein
the second advance signal is the color-coded signal; and
the control device is configured to display a countdown as the second advance signal.

* * * * *